US012746205B2

(12) United States Patent
Gram

(10) Patent No.: US 12,746,205 B2

(45) Date of Patent: Sep. 29, 2026

(54) METHOD FOR CONTROLLED RELEASE ORAL DRUG DELIVERY

(71) Applicant: Jes Tougaard Gram, Scottsdale, AZ (US)

(72) Inventor: Jes Tougaard Gram, Scottsdale, AZ (US)

( * ) Notice: Subject to any disclaimer, the term of this patent is extended or adjusted under 35 U.S.C. 154(b) by 328 days.

(21) Appl. No.: 18/610,261

(22) Filed: Mar. 20, 2024

(65) Prior Publication Data

US 2025/0295592 A1 Sep. 25, 2025

(51) Int. Cl.
*A61K 9/20* (2006.01)

(52) U.S. Cl.
CPC .................................. *A61K 9/2072* (2013.01)

(58) Field of Classification Search
None
See application file for complete search history.

(56) References Cited

U.S. PATENT DOCUMENTS

| | | | |
|---|---|---|---|
| 2007/0004204 A1 | 1/2007 | Fukazawa et al. | |
| 2018/0023588 A1 | 1/2018 | Van Der Kooi et al. | |
| 2020/0028974 A1 | 1/2020 | Chauhan | |
| 2020/0289747 A1* | 9/2020 | Imran | A61K 38/13 |

FOREIGN PATENT DOCUMENTS

WO WO 2013003824 A1 1/2013

OTHER PUBLICATIONS

Prinderre, et al., Advances in gastro retentive drug-delivery systems, Expert Opin. Drug Deliv., 8 (2011) pp. 1189-1203. (Year: 2011).*

* cited by examiner

*Primary Examiner* — Dominic Lazaro
(74) *Attorney, Agent, or Firm* — Edward J Challie

(57) ABSTRACT

The present invention discloses a method of enabling a better and more controlled drug release from an oral administered pill and/or an oral delivery device by using gravity adding weight/high density content to secure that the pill/device decent through the stomach fluids and come in close contact with stomach and/or intestine tissue as it dissolves/releases the drug enabling a better controlled absorption/transfer of the drug to the blood stream.

25 Claims, 4 Drawing Sheets

Fig.4
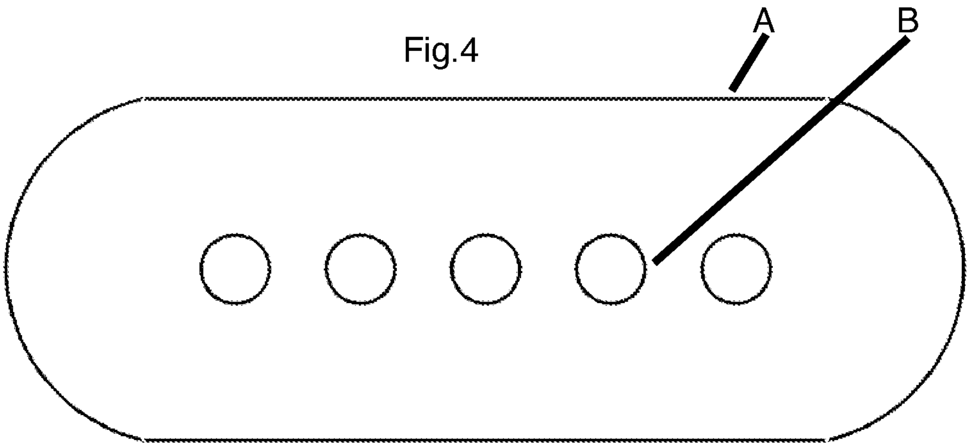
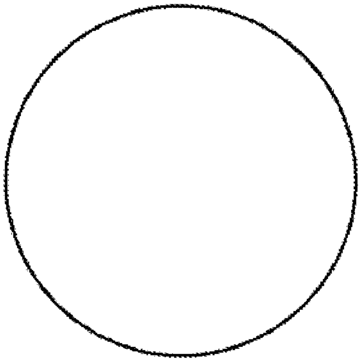
Fig.5
Fig.6
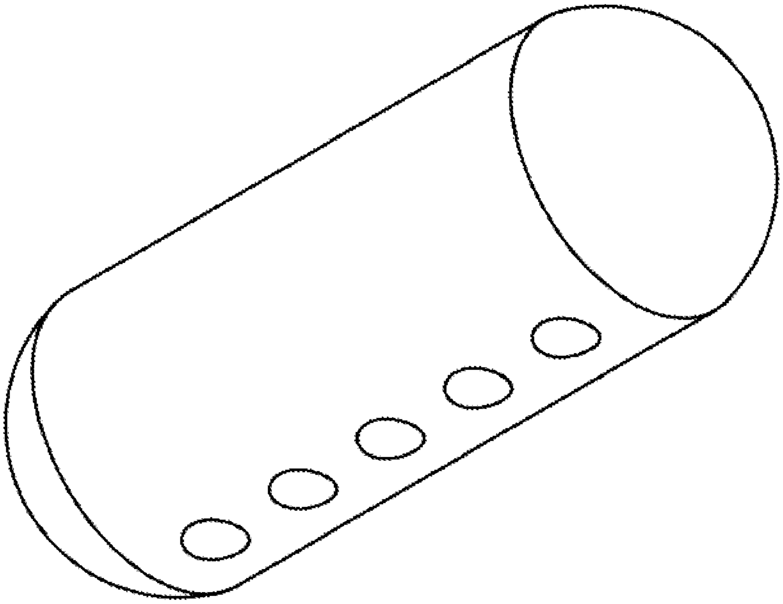

Fig.10
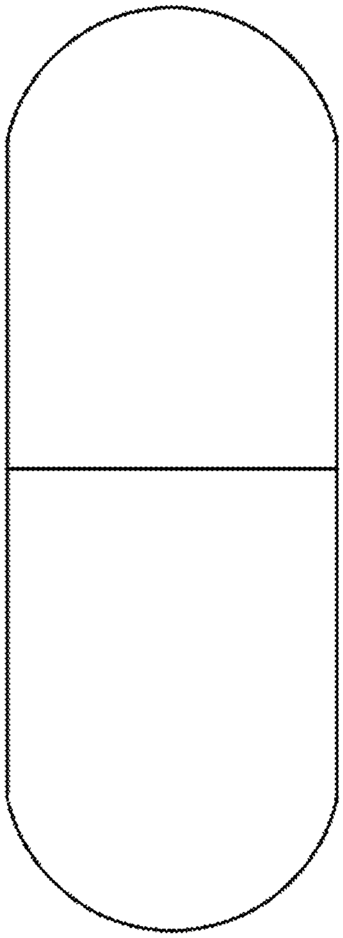
Fig.11
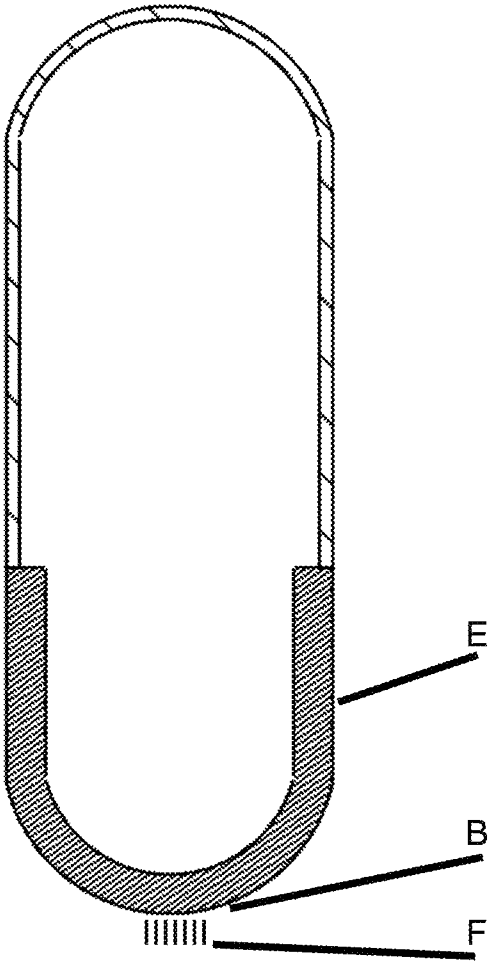
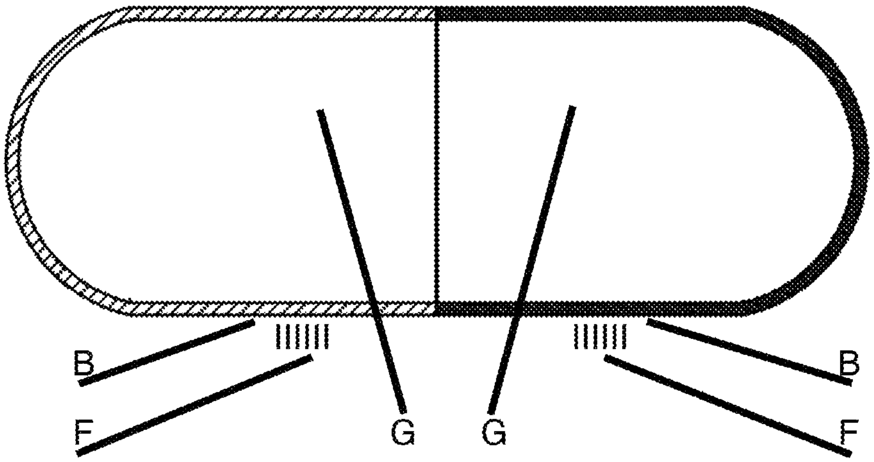
Fig.12

METHOD FOR CONTROLLED RELEASE ORAL DRUG DELIVERY

FIELD OF INVENTION

The present invention relates to a method enabling a better and more controlled drug release from an oral pill and/or delivery device introduced into the stomach of a living being.

BACKGROUND OF THE INVENTION

Oral drug administration remains the preferred route for patients and health care providers. Delivery of macromolecules through this route remains challenging because of limitations imposed by the transport across the gastrointestinal epithelium and the dynamic and degradative environment.

Therefore, a relatively large dose and high dosing frequency are required for oral dosage forms compared to administering a drug dose by injection.

Nevertheless, the oral delivery serves as a convenient dosage form for the patient and health care provider and can result in optimal therapeutic outcomes.

However, the efficacy of orally delivered drugs is limited because of the susceptibility of the drug compounds to proteolytic degradation in the gastrointestinal tract and the poor penetration of the often relatively large molecules across the epithelium.

A challenge for oral delivery is that the formulation can be prematurely exposed to the harsh gastrointestinal tract environment, which can cause it to break down before it reaches its intended target.

A gelatin capsule is commonly used to deliver oral formulations to avoid premature exposure of the formulations. Unfortunately, when gelatin dissolves, it becomes quite adherent, which can foul and interfere with the release of the formulation to the tissue surface.

Several approaches, such as adding protease inhibitors or penetration enhancers to drug formulations and nano/micro-technology solutions, are under preclinical and clinical evaluation, which may open new opportunities in the field of oral drug delivery.

Quick erosion of current oral drug delivery and its inability to attach to the tissue may result in a short residence time of the tablet and contribute to the low bioavailability of the drug.

Egalet has pioneered one of the world's first erosion-based delivery technologies to enable the controlled release of drugs through gradual erosion of a tablet.

U.S. patent application Ser. No. 2007/0042044 entitled: "Matrix Compositions for Controlled Delivery of Drug Substances."

The patent relates to the Egalet prolonged release technology. The composition described by the patent family is utilized for all the Egalet opioid products tested in clinical trials including the new improved tablet construction that has a very hard shell surrounding the erodible matrix containing the opioid.

Egalet's drug delivery platform, was designed to prevent easy extraction and to deter the abuse of medications via known routes of abuse, including chewing, snorting, and injecting.

The patient-friendly tablet consists of matrix and can add a shell or coat. By altering the composition of the shell and matrix, a variety of extended-release formulations can be produced.

The technology offers a predictable and tailored pharmacokinetic profile, lacks a significant food effect and alcohol dose dumping, and can be used with a broad range of opioids and non-opioids.

Contact time and distance from oral formulations or devices have been previously correlated with improvements in drug efficacy and reduce the need for high-frequency administration, thus motivating the development of systems capable of supporting transient immobilization.

Currently, the most used materials for this purpose are either too quick or too slow to adhere to tissue and they may also release toxic chemicals to induce inflammation.

Chemical-based adhesives, such as acrylic acid derivatives, cellulose derivatives, and alginate, need an abundant amount of hydrophilic functional groups to entangle and penetrate mucin: Hydrophilic functional groups enable the formation of numerous hydrogen bonds between the polymer and mucin.

Delivery of macromolecules remains challenging because of the transport across the gastrointestinal environment and some of the latest development of oral delivery systems combines physical microneedle and nonphysical enhancer modes of drug delivery enhancement for a macromolecule.

Such a microneedle system capable of prolonged gastric mucosa fixation is currently one of the development roads for controlled release of oral drug delivery solutions taken in the industry.

GLP-1, a major incretin hormone in humans, acts by numerous mechanisms like augmented insulin secretion (glucose-dependent), inhibition of glucagon release and suppressed hepatic gluconeogenesis. It also causes delayed gastric emptying, reduced appetite and energy intake.

Glucagon-like peptide-1 (GLP-1) is a gut-derived peptide produced by intestinal cells after ingestion of glucose, exerting glucose-lowering effects by augmenting insulin secretion through activating GLP-1 receptor.

Therefore, a class of peptides with similar structures to GLP-1 which can also stimulate GLP-1 receptor, known as glucagon-like peptide-1 receptor agonists (GLP-1RAs), were developed to improve glucose control for treatment of type 2 diabetes.

These drugs can be classified into two groups, long-acting (dulaglutide, albiglutide, semaglutide, liraglutide, and once-weekly exenatide) and short-acting (lixisenatide and twice-daily exenatide) regimens, based on the duration of action.

To date, a total of six medications including liraglutide, exenatide, dulaglutide, albiglutide, lixisenatide, and semaglutide have been approved by the US Food and Drug Administration (FDA) for use in the management of type 2 diabetes.

Recently, the first oral GLP-1 receptor agonist, which co-formulated semaglutide with the penetration enhancer sodium N-[8(2-hydroxybenzoyl) amino] caprylate (SNAC) in a tablet form, was approved for the treatment of type 2 diabetes.

SNAC has been shown to exhibit buffering action to increase local pH values in the stomach, resulting in lower protease activity and higher peptide stability. SNAC can promote the monomerization of semaglutide to improve the drug's solubility and absorption via the transcellular route.

Nevertheless, quick erosion of the pill, disintegration time and its inability to attach to the tissue may result in a short residence time of the tablet and contribute to the low bioavailability of the drug.

Also, a relatively large dose (10 mg or more) and high dosing frequency (once daily) are required for oral dosage forms compared to a once-weekly subcutaneous injection of semaglutide (1 mg per week); this may reduce patient adherence and increase treatment cost.

The oral pill is based on a Novo Nordisk invention U.S. Pat. No. 11,033,499 and relates to solid compositions comprising a GLP-1 peptide and a delivery agent, such as SNAC a salt of N-(8-(2-hydroxybenzoyl) amino) caprylic acid (NAC). NAC is acidic due to its carboxyl group. In some embodiments the delivery agent is an absorption enhancer. The structural formula of N-(8-(2-hydroxybenzoyl) amino) caprylate.

Semaglutide, a glucagon like peptide-1 (GLP-1) receptor agonist, is available as monotherapy in both subcutaneous as well as oral dosage form (first approved oral GLP-1 receptor agonist). It has been approved as a second line treatment option for better glycemic control in type 2 diabetes and currently under scrutiny for anti-obesity purpose.

Semaglutide, developed by Novo Nordisk, has been launched clinically and marketed as Ozempic® (subcutaneous injection, weekly-once dosing; available in 0.5, 1.0 mg dose) and Rybelsus® (oral tablets, once-daily dosing; available in 3, 7, 14 mg dose) making the oral dose 50-100 times higher than the injectable dose.

Both Ozempic and Rybelsus has been approved by USFDA, Health Canada, European Medicines Agency, Japanese Health ministry and is under scrutiny by several other regulatory authorities.

Studies with glucagon-like peptide-1 (GLP-1) have observed that this peptide modulates fluid intake and increases renal sodium excretion in healthy volunteers and in patients with diabetes mellitus type 2. on the effect of GLP-1 on thirst, water intake and on osmoregulation.

Cells have membranes which are permeable to water diffusion, but which do not allow salt to pass. Thus, only water can diffuse. This diffusion of water across a semi-permeable membrane is called osmosis.

The difference between diffusion and osmosis: Diffusion refers to the movement of molecules from an area of high concentration to an area of lower concentration. Osmosis is a type of diffusion specifically for water molecules moving across a semi-permeable membrane.

Cell membranes are an example of semi-permeable membranes. Cell membranes allow small molecules such as oxygen, water carbon dioxide and glucose to pass through, but do not allow larger molecules like sucrose, proteins, and starch to enter the cell directly.

A higher concentration of glucose in the intestine than the blood enables the glucose moves from high concentration in the small intestine to lower concentration in the body by diffusion.

Water is absorbed across the small intestine in the absence of external driving forces. However, it has been established that water transport is secondary to active sodium transport. In the upper intestine both sodium and water absorption are largely dependent on the presence of D-glucose.

The link between active sodium transport and glucose is the coupled transport of sodium and glucose across the brush border membrane of enterocytes by the Na+/glucose cotransporter (SGLT1).

Na+ that enters the cells with glucose is pumped out towards the blood by 3Na+/2K+ pumps on the basolateral membrane, and glucose passes out across the basolateral membrane by facilitated diffusion, the net result being that glucose and sodium are transported across the epithelium.

The coupling between Na+, glucose, and water transport is less well understood. It is commonly thought that Na+ transport increases the local osmotic pressure in the lateral intercellular spaces, and that this in turn generates osmotic water flow across the epithelium.

Recent work suggests a more direct link between Na+, glucose, and water transport; that is, water is co-transported along with Na+ and sugar through SGLT1. Showing evidence for Na+/glucose/water cotransport.

Contact time and distance from oral formulations or devices have been previously correlated with improvements in drug efficacy and reduce the need for high-frequency administration, thus motivating the development of systems capable of supporting transient immobilization.

Time-release drugs use a special technology to release small amounts of the medication into a person's system over a long period of time. This is also referred to as sustained release, extended release, or controlled release. These tend to come in pill form and are simply made to be more potent but dissolve slowly. Sustained release technology is a class of technology characterized by slowly releasing specific active substances into a target medium to keep a certain concentration in the system within valid time.

Most time-release drugs are now formulated with the active pharmaceutical ingredient embedded in a matrix of insoluble materials such as acrylics or chitin. Here the mechanism relies upon the dissolving drug finding its way out through pores. Some sustained release drug forms dissolve the active into a matrix.

The basic mechanisms that control the release of the drug molecules through the polymeric layer are osmosis, diffusion, chemical degradation, swelling and dissolution, with diffusion playing a dominant role in many controlled release systems.

A variety of specific materials may be used for the biodegradable shells, including biodegradable metals, such as magnesium, iron, and zinc. Biodegradable polymers will also be useful, including, for example, poly lactic acid (PLA), poly lactic-co-glycolic acid (PGLA) and various sugars such as maltose, sucrose and the like.

Bioabsorbable metals are based on magnesium (Mg), iron (Fe) and zinc (Zn), as their degradation products are biocompatible, magnesium alloys being the most popular. They have been used to develop bioabsorbable structural implants, including plates, screws, and bone anchors. Ceramics are non-metallic, often crystalline oxides, of commonly nitride or carbide materials. Bioabsorbable ceramics include a variety of materials, such as calcium and carbon phosphates, alumina, and hydroxyapatite (HAp).

Further according to one or more embodiments the shell may comprise multiple layers of the same or different materials with the layers configured to degrade at different rates e.g., hours vs days or longer.

The human stomach is capable of absorbing most acidic drugs and the very weakly basic drugs. Salicylic acid, aspirin, thiopental, secobarbital and antipyrine, which are undissociated in the acidic gastric contents, were readily absorbed.

Phenol red, quinine, ephedrine and aminopyrine, which are almost completely ionized in acid solution were not absorbed. These results are compatible with the hypothesis that drugs are absorbed by passive diffusion of their lipid soluble undissociated form.

Many drugs may be absorbed by the human stomach as rapidly or more rapidly than ethyl alcohol.

Although the stomach absorbs few of the products of digestion, it can absorb many other substances, including glucose and other simple sugars, amino acids, and some fat-soluble substances.

The pH of the gastric contents determines whether some substances are absorbed. At a low pH, for example, the environment is acidic, and aspirin is absorbed from the stomach almost as rapidly as water, but, as the pH of the stomach rises and the environment becomes more basic, aspirin is absorbed more slowly.

Acidity regulators, also known as acidulants, are a type of food additive commonly used to regulate the acidity or alkalinity of foods and beverages.

Acidity regulators include various types of acids such as lactic acid, malic acid, fumaric acid, citric acid, tartaric acid, phosphoric acid, and sodium citrate. These acids are used in a wide range of food and beverage products to provide a sour or acidic taste, to control the pH level, and to act as preservatives.

Commonly used acidulants are acetic acid (E260), lactic acid (E270), malic acid (E296), fumaric acid (E297), citric acid (E330), tartaric acid (E334), phosphoric acid (E338) and succinic acid (E363)

Water moves freely from the gastric contents across the gastric mucosa into the blood. The net absorption of water from the stomach is small, however, because water moves just as easily from the blood across the gastric mucosa to the lumen of the stomach.

The absorption of water and alcohol can be slowed if the stomach contains foodstuffs and especially fats, probably because gastric emptying is delayed by fats, and most water in any situation is absorbed from the small intestine.

The rate of emptying of the stomach depends upon the physical and chemical composition of the meal. Fluids empty more rapidly than solids, carbohydrates more rapidly than proteins, and proteins more rapidly than fats.

When the food is triturated, it can pass through the pylorus; the physical nature, particle size, fat and caloric content of food alter the emptying rate. The rate of liquid emptying is much more rapid (time taken to empty 50%, $T_{1/2}$ is ~20 minutes) compared to emptying of solids ($T_{1/2}$ is ~120 minutes)

When food particles are sufficiently reduced in size and are nearly soluble and when receptors in the duodenal bulb (the area of attachment between the duodenum and the stomach) have a fluidity and a hydrogen ion concentration of a certain level, the duodenal bulb and the second part of the duodenum relax, allowing emptying of the stomach to start.

During a duodenal contraction, the pressure in the duodenal bulb rises higher than that in the antrum. The pylorus prevents reflux into the stomach by shutting.

The vagus nerve has an important role in the control of emptying, but there is some indication that the sympathetic division of the autonomic nervous system is also involved.

Several of the peptide hormones of the digestive tract also influence intragastric pressure and gastric movements. Glucagon-like peptide 1 (GLP-1) is a physiological incretin hormone from the lower gastrointestinal tract, partially explaining the augmented insulin response after oral compared to intravenous glucose administration in humans.

The major effects on gastric emptying result from actions of incretins, particularly GIP, GLP-1 and PYY, the duodenal and pancreatic hormones, motilin, glucagon, and amylin, and the gastric orexigenic hormones, ghrelin, and motilin.

All these hormones delay gastric emptying, except for ghrelin and motilin which accelerate gastric emptying. These effects on gastric emptying parallel the effects of the hormones on satiation (by those retarding emptying) and increase appetite by those that accelerate emptying.

The small intestine is the principal organ of the digestive tract. The primary functions of the small intestine are mixing and transporting of intraluminal contents, production of enzymes and other constituents essential for digestion, and absorption of nutrients.

Most of the processes that solubilize carbohydrates, proteins, and fats and reduce them to relatively simple organic compounds occur in the small intestine.

The small intestine, which is 670 to 760 cm (22 to 25 feet) in length and 3 to 4 cm (about 2 inches) in diameter, is the longest part of the digestive tract. It begins at the pylorus, the juncture with the stomach, and ends at the ileocecal valve, the juncture with the colon.

The main functional segments of the small intestine are the duodenum, the jejunum, and the ileum.

Drug delivery technologies have been proven to improve treatment outcomes in many ways, including enhancing therapeutic efficacy, reducing toxicity, increasing patient compliance, and enabling entirely new medical treatments.

As the therapeutic landscape has evolved from small-molecule drugs to a new generation of therapeutics including proteins, peptides, monoclonal antibodies, nucleic acids, and even live cells, drug delivery technologies have also evolved to meet their unique delivery needs.

Generally, food stays in the stomach between 40 minutes to two hours, before spending another 40 minutes to two hours in the small bowel. It then spends around five hours in the small intestine, before passing through the colon, which can take anywhere between 10 to 59 hours.

The gastric mucosa secretes 1.2 to 1.5 liter of gastric juice per day. Gastric juice renders food particles soluble, initiates digestion (particularly of proteins), and converts the gastric contents to a semiliquid mass called chyme, thus preparing it for further digestion in the small intestine.

Gastric contents have a density close to water ("≈1.004 g/cm3). Pure table salt (NaCl) is ("≈2.17 g/cm3) while pure table sugar (sucrose) is ("≈1.587 g/cm3).

Sugar is more soluble in water than salt. In an ionic compound such as table salt, the ions are held together by strong electrostatic forces of attraction.

However, when water dissolves sugar, it separates the individual sugar molecules by disrupting the relatively weak intermolecular forces of attraction between the sugar molecules.

The size of the sugar molecule is greater than that of the salt molecule. Thus, a single sugar molecule can attract more water molecules than the table salt leading to its faster dissolution in water.

Metals important to our health include calcium, chromium, copper, iron, magnesium, manganese, molybdenum, potassium, sodium, and zinc. Gold is a particularly non-reactive element and is not absorbed during the digestion process, so it is safe to eat. However, there are no nutritional or health benefits associated with its consumption.

An edible noble metal is any precious metal that can be safely consumed. It most often refers to gold and silver. These metals are considered 'noble' as they do not oxidize or corrode in moist air, unlike many others. This makes them perfect for use in food items as most contain a high amount of moisture.

A noble metal is ordinarily regarded as a metallic chemical element that is generally resistant to corrosion and is usually found in nature in its raw form. The noble metals are gold, silver, platinum, rhodium, iridium, palladium, ruthenium, and osmium, with rhenium included on some lists.

E.g., the density of Zinc is 7.13 g/cm3 the density of iron is 7.874 g/cm3 whereas the density of silver is 10.49 g/cm3. Gold has a density of 19.3 g/cm3.

There are many techniques delivering a therapeutic substance to the target site in a sustained or controlled release fashion.

In recent years scientific and technological advancements have been made in the research and development of rate-controlled oral drug delivery systems by overcoming physiological adversities, such as short gastric residence times and unpredictable gastric emptying times.

Several approaches for a gastroprotective drug delivery system offers several advantages besides providing better bioavailability to poorly absorbed drugs and a required release profile thus attracting interest of pharmaceutical formulation scientists.

Insulin helps blood sugar enter the body's cells so it can be used for energy. Insulin also signals the liver to store blood sugar for later use. Blood sugar enters cells, and levels in the bloodstream decrease, signaling insulin to decrease too.

Glucagon is a glucoregulatory peptide hormone that counteracts the actions of insulin by stimulating hepatic glucose production and thereby increases blood glucose levels.

Antacids are relative simply assembled salts and salt-like compounds which neutralize acids. This neutralization reactions lead to several products (other salts, water, and possibly carbon dioxide), resulting in steps, like hydrolysis and precipitations of insoluble. The antacids act by neutralizing the acid in the stomach and by inhibiting pepsin, which is a proteolytic enzyme.

Most antacids contain at least one of the following key ingredients: calcium carbonate, magnesium hydroxide, aluminum hydroxide and/or sodium bicarbonate. These and similar ingredients can help to neutralize the stomach's acid.

The pH of stomach acid typically falls between 1.5 and 3.5. The stomach becomes alkaline when utilizing too much hydrogen carbonate, further stimulating the creation of acids. Antacids often have an alkaline pH of around 10, which neutralizes the stomach acid.

Therefore, choosing these insoluble metal hydroxides that do not raise pH levels over neutrality include substances like magnesium (having a density 1.738 g/cm3) and aluminum hydroxide (having a density 2.42 g/cm3) or sodium hydrogen carbonate (having a density 2.159 g/cm3).

A roly-poly toy, round-bottomed doll, tilting doll, tumbler, wobbly man, or wobble doll is a round-bottomed toy, usually egg-shaped, that tends to right itself when pushed at an angle, and does this in seeming contradiction to how it should fall. The toy is typically hollow with a weight inside the bottom hemisphere.

The placement of this weight is such that the toy has a center of mass below the center of the hemisphere, so that any tilting raises the center of mass. When such a toy is pushed over, it wobbles for a few moments while it seeks the upright orientation, which has an equilibrium at the minimum gravitational potential energy.

It is apparent now that numerous methods and systems are developed in the prior art that are adequate for various purposes. Furthermore, even though these inventions may be suitable for the specific purposes to which they address, accordingly, they would not be suitable for the purposes of the present invention as heretofore described.

Thus, a method of using gravity enabling a faster delivery and enhancing a controlled drug release from an oral drug delivery pill and/or device is novel with a large market potential.

SUMMARY OF THE INVENTION

The method according to the invention comes in the form of an oral administrated controlled release pill and/or device that position itself in the stomach and/or intestine tissue lining the pill and/or device having a higher density then the gastric contents that has a density close to water ("≈1.004 g/cm3) and potentially also a weight composition having a placement of the highest density/weight in such a way that the pill/device has a center of mass below the center of the hemisphere, so that any tilting raises the center of mass having its main delivery function at the bottom surface in contact with the tissue. This could be combined with a protective cover/layer over the low-density/weight part of the pill/device facing away from the tissue contact point protecting the drug content from the stomach aggressive gastric content.

Drug delivery and targeted treatments with antibiotic, pain reliver or other oral delivered treatment options could be orally administered much faster and more accurately if the pill/device, having a higher density than the stomach fluids, allowing it to pass through the hostile environment of the stomach to be released against the tissue in the stomach and/or in the intestine at an expedited time limiting the deluding and/or damaging of the drug content by the stomach fluids.

The present invention discloses a method of enabling a better and more controlled drug release from an oral administered pill and/or an oral drug delivery device by using gravity adding weight/higher density content e.g., salts, sugars, or even metals to secure that the pill/device decent through the stomach fluids and come in close contact with stomach tissue and/or intestine tissue as it dissolves/releases the drug enabling a better controlled absorption/transfer of the drug to the blood stream.

Introducing a higher density carrier compound/additive in the pill and/or the oral drug delivery device ensuring weight/density that enables the decent in the stomach fluids, to a point of close contact with stomach and/or intestine tissue minimizing the proteolytic degradation in the gastrointestinal tract and improving the chance of penetration of the often relatively large molecules across the epithelium.

The close tissue contacts while dissolving/releasing the drug content improving the pathway of the drug to the blood stream. Enabling enhanced drug transfer in the stomach and/or in the intestine surface tissue due to the lesser deluded drug concentration not having to mix with as much stomach fluids and enduring as much degradation before being able to be absorbed into the blood stream.

The method in accordance with the invention enables a better and more controlled drug release from an oral administered pill and/or an oral drug delivery device, having a combined bulk density of more than the normal gastric stomach contents density close to water ("≈1.004 g/cm3) enabling it to sink to the bottom of the gastric stomach thereby meeting the tissue of the stomach.

The method in accordance with the invention enables a better and more controlled drug release from an oral administered pill and/or an oral drug delivery device, having a combined bulk density of more than 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5 g/cm3 or even an higher bulk density e.g. based on a high noble metal content like silver and gold and/or biodegradable metals and/or ceramics.

The method in accordance with the invention enables a better and more controlled drug release from an oral administered pill and/or an oral drug delivery device, having a combined bulk density of more than the normal gastric stomach contents could also be encapsuled in whole or in part with a e.g., a gelatin coating and/or container capsule/ cover for an initial protection of the pill/device content and/or delivery area during its decent in the stomach.

The method in accordance with the invention could also have at least one barrier layer protecting the area of the pill/device facing away and not in contact with the tissue contact area enabling a more controlled delivery of the content, e.g., having the protective barrier layer made from a slower biodegradable material, a compound or even plastic or other material that would naturally leave the body with other waste products after delivering its content.

The method in accordance with the invention the pill/device could have a higher weight at its bottom/delivery hemisphere. The placement of this weight is such that the pill/device has a center of mass below the center of the hemisphere, so that any tilting raises the center of mass.

When such a pill/device is introduced into the stomach having a center of mass below the center of the hemisphere, it will wobble for a few moments while it seeks the upright orientation during its decent in the stomach and/or intestines, having an equilibrium at the minimum gravitational potential energy.

Thereby positioning the delivery area of the pill/device against the stomach tissue when the decent stops while the protective coating protect the rest of the pill/device against the aggressive stomach fluids enabling e.g., a better controlled delivery by diffusion and/or osmosis.

The gravity effect of the high density/weighted pill/delivery device works regardless of how the patient is positioned, so even if the patient is laying down the high density/weighted pill/delivery device will position itself against the tissue.

The additional weight/higher density would also slow the speed of the pill/device traveling through the stomach and/or intestines ensuring a more consistent drug delivery having a relative consistent tissue contact before being fully dissolved and/or the remaining part of the pill/device leaving the body.

The method in accordance with the invention the pill/device could have traction enhancers like little bumps, track patterns or even micro needles to slow its movements over the tissue in the stomach and/or intestines at its bottom/delivery hemisphere at the delivery area location close to/under the placement of its weight/density of the pill/device that has a center of mass below the center of the hemisphere.

Such traction enhancers could also be combined with hydrophobic and/or hydroscopic surfaces as well as chemical-based adhesives, such as acrylic acid derivatives, cellulose derivatives, and alginate, that need an abundant amount of hydrophilic functional groups to entangle and penetrate mucin. Including hydrophilic functional groups that can enable the formation of numerous hydrogen bonds between the polymer and mucin.

The method in accordance with the invention the pill/device could have a higher weight/density at its bottom/delivery hemisphere. The placement of this weight/density is such that the pill/device has a center of mass below the center of the hemisphere and could include sugars, salts, and even metals ensuring the heigh density/weight in the pill/device.

This so that any tilting raises the center of mass and reposition the delivery area of the pill/device against the tissue enabling the continues absorption of the drug into the blood stream e.g., improved through osmoses and/or diffusion using salt and/or sugars in various combinations to help a given component/drug to cross into the blood stream.

The method in accordance with the invention the pill/device could also have a basic content/composition being released with the drug to counter the aggressive stomach fluids in the delivery area.

The method in accordance with the invention the pill/device could also have an acidic content/composition being released with the drug to compensate for a low pH in the delivery area. This because e.g., if the environment is acidic an aspirin is absorbed from the stomach almost as rapidly as water, but as the pH of the stomach rises and the environment becomes more basic, aspirin is absorbed more slowly.

The method in accordance with the invention the pill/device could be carrying a content/composition in multiple layers and/or delivery areas where an acidic and/or basic additive would support how the content was absorbed in each given area e.g., the stomach and/or in the intestines.

The method in accordance with the invention the pill/device could be carrying a content/composition of therapeutic additions from small-molecule drugs to a new generation of therapeutics including proteins, peptides, hormones, monoclonal antibodies, nucleic acids, vitamins, sleep aid and even live cells, drug delivery designed to meet their unique delivery needs.

The method in accordance with the invention the pill/device could also have an opening/exposed area in its design enabling the aggressive stomach fluids to separate the pill in two e.g., resulting in different weight/density.

The method in accordance with the invention the pill/device could also have an opening/exposed area in its design enabling the aggressive stomach fluids to separate the pill/device in two or more parts e.g., resulting in a change in the placement of the weight/density is such a way that the pill/device now has a new center of mass below the center of the hemisphere potentially also activating the drug delivery area of the pill/device.

The method in accordance with the invention the pill/device could also include multiple drug delivery areas and/or release steps delivering the same and/or different contents, e.g., as the pill/device dissolves and/or the pill/device separates.

This could e.g., be achieved by the pill/device having designated separation/break point e.g., an hourglass kind of shape where the center of mass would be in the area with the smallest diameter first laying on the stomach tissue.

This area could have a lessor or no protective layer against the stomach fluids that would dissolve this area separating the pill/device into two new shaped drug delivery units standing on the stomach tissue, both now having e.g., the same and/or a different weight/density.

The separation/dissolving of the pill/device could also be focused on the heavy content leaving the pill/device at a bulk density close to the sastric contents have a density close to water ("≈1.004 g/cm3). Thereby helping the pill/device movement to the intestines.

It could also be a relatively easy dissolving container capsule carrying at least one pill/device with a center of mass positioning its delivery area against the stomach and/or insistent tissue when it releases from the container capsule and/or this dissolves in whole or in part releasing at least one pill/device to position itself and/or delivery area against the tissue for delivery of its content.

The method in accordance with the invention the pill/device could also include a basic content/composition e.g., by choosing to include an insoluble metal hydroxide that do not raise pH levels over neutrality, this includes substances like magnesium (having a density 1.738 g/cm3) and aluminum hydroxide (having a density 2.42 g/cm3) or sodium hydrogen carbonate (having a density 2.159 g/cm3).

The method in accordance with the invention the pill/device could also include a hormone content/composition e.g., by choosing to include at least one of hormones that has a major delaying effect on gastric emptying result from actions of incretins, particularly GIP, GLP-1 and PYY, the duodenal and pancreatic hormones, motilin, glucagon, and amylin, and the gastric orexigenic hormones.

The method in accordance with the invention the pill/device could also include a hormone content/composition e.g., by choosing to include at least one of hormones that has a major accelerating effect on gastric emptying result from actions of incretins, e.g., like ghrelin, and motilin.

The method in accordance with the invention the pill/device could also include a combination of salt/sodium and sugar/glucose content/composition e.g. by choosing to include Na+ that enters the cells with glucose and is pumped out towards the blood by 3Na+/2K+ pumps on the basolateral membrane, and glucose passes out across the basolateral membrane by facilitated diffusion, the net result being that glucose and sodium are transported across the epithelium also enabling an better and expedited transport of the drug content of the pill/device e.g., pain medication or hormones like the glucagon-like peptide 1 (GLP-1) a physiological incretin hormone from the lower gastrointestinal tract.

The method in accordance with the invention the pill/device could also have a salt content/composition of less than 50%

The method in accordance with the invention the pill/device could also have a salt content/composition of more than 50%

The method in accordance with the invention the pill/device could also have a liquid content/composition being released in the delivery area after reaching stomach tissue and/or intestine tissue.

The method in accordance with the invention the pill/device could also have a granulate and/or paste content/composition being released in the delivery area after reaching stomach tissue and/or intestine tissue.

The method in accordance with the invention the pill/device could have a multiple drug delivery capability with a separation layer/wall and/or chambers enabling separation of combination drugs that needs to be kept separated until the time of release.

The method in accordance with the invention the pill/device could have a higher weight at its bottom/delivery hemisphere and a lower weight at the top hemisphere, thereby helping the pill/device to achieve the right delivery position.

The method in accordance with the invention the pill/device could be introduced into a protective cover protecting the content against the stomach fluids, the cover being heavy enough to insure its decent through the stomach fluids and having a center of mass positioning its delivery area against the stomach and/or insistent tissue so the content releases from the protective cover on to the tissue as it dissolves.

The method in accordance with the invention the pill/device contains a combination of a liquid and/or a dry content kept separated until time of delivery, the dry content e.g., being a solid, a granulate or a paste.

Other objectives and aspects of the invention will become apparent from the following detailed description, taken in conjunction with the accompanying drawings, which illustrate, by way for example, the features in accordance with embodiments of the invention.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

Although, the invention is described above in terms of various exemplary embodiments and implementations, it should be understood that the various features, aspects, and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

The presence of broadening words and phrases such as "one or more," "at least," "but not limited to" or other like phrases in some instances shall not be read to mean that the narrower case is intended or required in instances where such broadening phrases may be absent.

BRIEF DESCRIPTION OF DRAWINGS

The accompanying drawings illustrate various embodiments of systems, methods, and embodiments of various other aspects of the disclosure. Any person with ordinary skills in the art will appreciate that the illustrated element boundaries (e.g., boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another and vice versa. Furthermore, elements may not be drawn to scale. Non-limiting and non-exhaustive descriptions are described with reference to the following drawings. The components in the figures are not necessarily to scale, emphasis instead being placed upon illustrating principles. Furthermore, the drawings may contain text or captions that may explain certain embodiments of the present invention. This text is included for illustrative, non-limiting, explanatory purposes of certain embodiments detailed in the present invention. In the drawings:

Embodiments of the invention are described with reference to the following figures. The same numbers are used throughout the figures to reference like features and components. The features depicted in the figures are not necessarily shown to scale. Certain features of the embodiments may be shown exaggerated in scale or in somewhat schematic form, and some details of elements may not be shown in the interest of clarity and conciseness.

FIG. 4 illustrates a bottom/tissue contact area view of a high-density/weight assembled/compounded pill/device according to the method in the present invention having a heavy load/high density at the bottom hemisphere to secure its position and having delivery area/holes for releasing its content.

FIG. 5 illustrates an end view of an assembled/compounded pill/device having a higher density/weight at the bottom horizontal hemisphere of the pill/device according to the method in the present invention.

FIG. 6 illustrates an angled view of an assembled/compounded pill/device having a higher density/weight at the bottom horizontal hemisphere of the pill/device having a side delivery area according to the method in the present invention.

FIG. 10 illustrates a vertical assembled protective content delivery carrier in accordance with the present invention.

FIG. 11 illustrates a vertical protective content delivery carrier having a higher density/weight at the bottom vertical hemisphere of the delivery device with its delivery area in the higher density/weight area where the content is getting delivered/dissolved according to the method in the present invention.

FIG. 12 illustrates multi compartment/chamber drug delivery device having a higher density/weight at the bottom vertical hemisphere and coated/protected in one or more layers having a delivery area where the content can dissolve e.g., osmoses and/or diffusion can take place in accordance with the present invention.

DETAILED DESCRIPTION OF THE INVENTION

Figure 1:
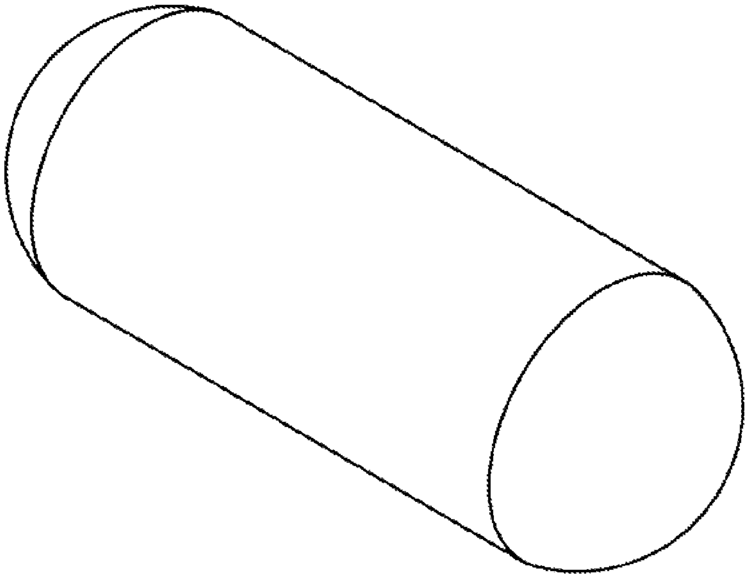
FIG. 1 illustrates a high-density/weight uniform compounded pill according to the method in the present invention.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein.

The general principles defined herein may be applied to other embodiments and applications without departing from the spirit and scope of the invention. Also, the terminology and phraseology used is for the purpose of describing exemplary embodiments and should not be considered limiting.

Thus, the present invention is to be accorded the widest scope encompassing numerous alternatives, modifications, and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "units" represents the dimension in any units such as centimeters, meters, inches, foots, millimeters, micrometer and the like and forms thereof, are not necessarily limited to members in a list with which the words may be associated.

In the description and claims of the application, each of the words "comprise", "include", "have", "contain", and forms thereof, are not necessarily limited to members in a list with which the words may be associated.

Thus, they are intended to be equivalent in meaning and be open-ended in that an item or items following any one of these words is not meant to be an exhaustive listing of such item or items or meant to be limited to only the listed item or items.

It should be noted herein that any feature or component described in association with a specific embodiment may be used and implemented with any other embodiment unless clearly indicated otherwise.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items from the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible.

For example, substitutions, additions, or modifications may be made to the elements illustrated in the drawings, and the methods described herein may be modified by substituting, reordering, or adding stages to the disclosed methods.

Accordingly, the following detailed description does not limit the disclosure. Instead, the proper scope of the disclosure is defined by the appended claims. The present invention contains headers. It should be understood that these headers are used as references and are not to be construed as limiting upon the subjected matter disclosed under the header.

This specification includes references to "one embodiment" or "an embodiment." The appearances of the phrases "in one embodiment" or "in an embodiment" do not necessarily refer to the same embodiment. Particular features, structures, or characteristics may be combined in any suitable manner consistent with this disclosure.

The presence of broadening words and phrases such as "one or more," "at least," "but not limited to" or other like phrases in some instances shall not be read to mean that the narrower case is intended or required in instances where such broadening phrases may be absent.

It must also be noted that as used herein and in the appended claims, the singular forms "a," "an," and "the" include plural references unless the context dictates otherwise. Although any systems and methods similar or equivalent to those described herein can be used in the practice or testing of embodiments of the present disclosure, the preferred, systems and methods are now described.

FIG. 1 illustrates a high-density/weight uniform compounded pill according to the method in the present invention.

Figure 2:
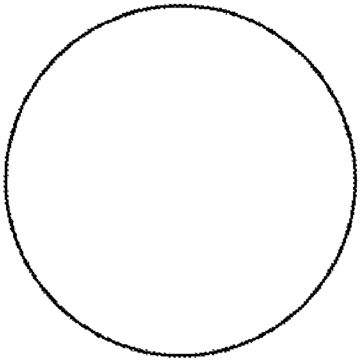
FIG. 2 illustrates an end view of a uniform high-density/weight compounded pill/device according to the method in the present invention.

FIG. 2 illustrates an end view of a uniform high-density/weight compounded pill/device according to the method in the present invention.

Figure 3:
FIG. 3 illustrates a side view of an assembled uniform high-density/weight compounded pill/device according to the method in the present invention.

FIG. 3 illustrates a side view of an assembled uniform high-density/weight compounded pill/device according to the method in the present invention.

FIG. 4 illustrates a bottom/tissue contact area view of a high-density/weight assembled/compounded pill/device A according to the method in the present invention having a heavy load/high density at the bottom hemisphere to secure its position and having delivery area/holes B for releasing its content.

FIG. 5 illustrates an end view of an assembled/compounded pill/device having a higher density/weight at the bottom horizontal hemisphere of the pill/device according to the method in the present invention.

FIG. 6 illustrates an angled view of an assembled/compounded pill/device having a higher density/weight at the bottom horizontal hemisphere of the pill/device having a side delivery area according to the method in the present invention.

Figure 7:
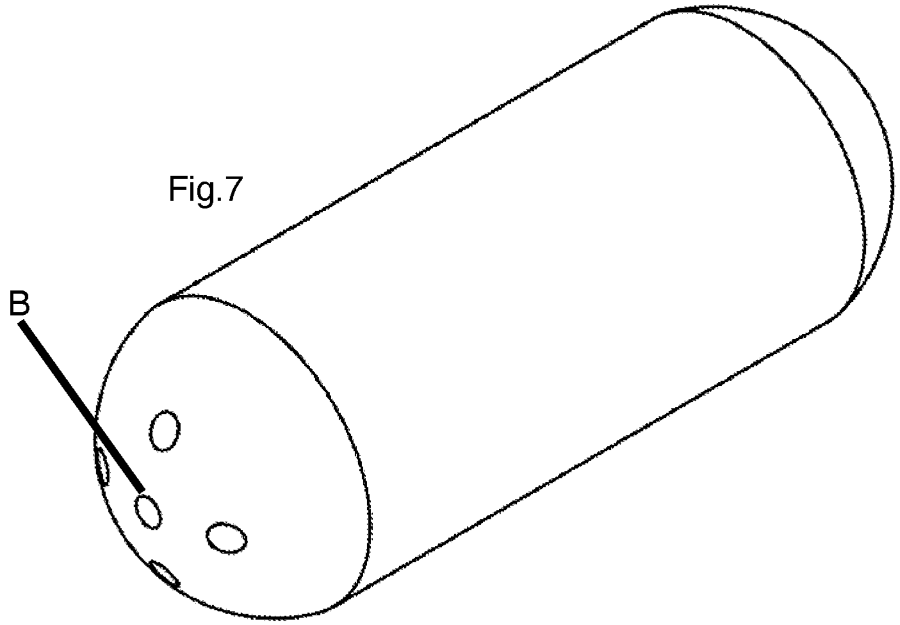
FIG. 7 illustrates an angled view of an assembled/compounded pill/device having a higher density/weight at the bottom vertical hemisphere of the pill/device having an end delivery area according to the method in the present invention.

FIG. 7 illustrates an angled view of an assembled/compounded pill/device having a higher density/weight at the bottom vertical hemisphere of the pill/device having an end delivery area B according to the method in the present invention.

Figure 8:
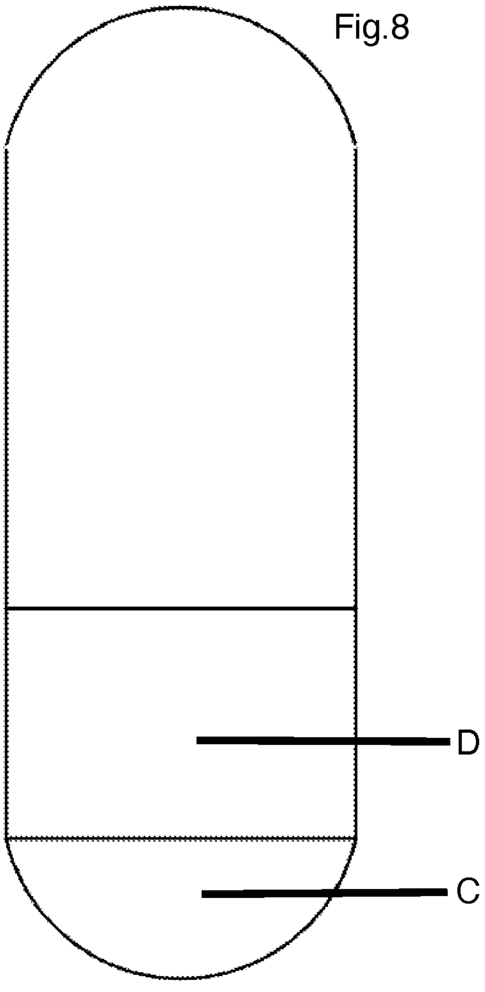
FIG. 8 illustrates a multi-layer assembled/compounded pill and/or device after the method in accordance with the present invention having the option to release/deliver its first content and/or heavy/high density ballast before giving access to the new exposed delivery area.

FIG. 8 illustrates a multi-layer assembled/compounded pill and/or device after the method in accordance with the present invention having the option to release/deliver its first content and/or heavy/high density ballast C before giving access to the new exposed delivery area D.

Figure 9:
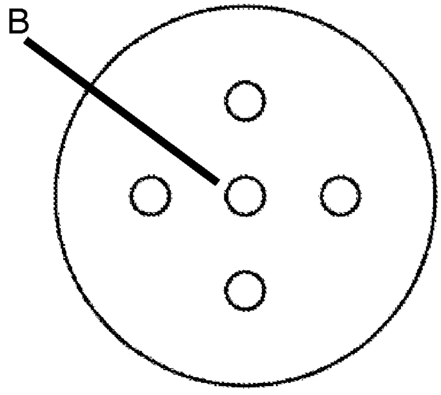
FIG. 9 illustrates an end view of an assembled/compounded pill/device having a higher density/weight at the bottom vertical hemisphere of the pill/device having its delivery area in the form of five holes according to the method in the present invention.

FIG. 9 illustrates an end view of an assembled/compounded pill/device having a higher density/weight at the bottom vertical hemisphere of the pill/device having its delivery area B in the form of five holes according to the method in the present invention.

FIG. 10 illustrates a vertical assembled protective content delivery carrier in accordance with the present invention.

FIG. 11 illustrates a vertical protective content delivery carrier having a higher density/weight at the bottom vertical hemisphere of the delivery device E with its delivery area B in the higher density/weight area where the content is getting delivered/dissolved F according to the method in the present invention.

FIG. 12 illustrates multi compartment/chamber G drug delivery device having a higher density/weight at the bottom vertical hemisphere and coated/protected in one or more layers having a delivery area B where the content can dissolve F, e.g., osmoses and/or diffusion can take place in accordance with the present invention.

While illustrative implementations of the application have been described in detail herein, it is to be understood that the inventive concepts may be otherwise variously embodied and employed, and that the appended claims are intended to be construed to include such variations, except as limited by the prior art.

Reference throughout this specification to "one implementation" or "an implementation" means that a particular feature, structure, or characteristic described in connection with the implementation is included in at least one implementation of the present invention.

Thus, the appearances of the phrases "in one implementation" or "in some implementations" in various places throughout this specification are not necessarily all referring to the same implementation. Furthermore, the particular features, structures, or characteristics may be combined in any suitable manner in one or more implementations.

Systems and methods describing the present invention have been described. It will be understood that the descriptions of some embodiments of the present invention do not limit the various alternative, modified, and equivalent embodiments which may be include within the spirit and scope of the present invention as defined by the appended claims.

Furthermore, in the detailed description above, numerous specific details are set forth to provide an understanding of various embodiments of the present invention. However, some embodiments of the present invention may be practiced without these specific details. In other instances, well known methods, procedures, and components have not been described in detail so as not to unnecessarily obscure aspects of the present embodiments.

The invention claimed is:

1. A method of enhancing targeted absorption of a therapeutic composition from an orally administered pill or oral drug delivery device, comprising:

incorporating a high-density ballast into a delivery region of the pill or device such that a center of mass is positioned to orient the delivery region toward gastric or intestinal tissue upon descent in gastric fluids;

wherein the pill or device contains the therapeutic composition;

wherein the orientation of the pill or device provides prolonged localized exposure of the therapeutic composition at a mucosal surface, thereby reducing proteolytic degradation and enhancing therapeutic uptake; and optionally providing a protective barrier outside the delivery region to shield non-delivery surfaces from gastric degradation.

2. The method of claim 1, wherein the pill or device contains sufficient ballast to descend through gastric fluids until contacting stomach tissue.

3. The method of claim 1, wherein ballast is distributed throughout the pill or device in an amount effective to promote descent through gastric fluids until contacting tissue.

4. The method of claim 1, wherein ballast is positioned off-center within the pill or device to control orientation during descent through gastric fluids and upon contact with tissue.

5. The method of claim 1, wherein the ballast produces a center of mass below a geometric center of the device such that tilting causes a self-righting movement that repositions the delivery region toward tissue.

6. The method of claim 1, wherein the protective barrier comprises a substantially biodegradable material.

7. The method of claim 1, wherein the therapeutic composition further comprises sodium and glucose in amounts effective to enhance transport of the therapeutic composition across gastrointestinal tissue.

8. The method of claim 7, wherein the concentration of sodium exceeds the concentration of glucose.

9. The method of claim 7, wherein the concentration of glucose exceeds the concentration of sodium.

10. The method of claim 1, wherein the therapeutic composition comprises one or more agents selected from proteins, peptides, hormones, monoclonal antibodies, nucleic acids, vitamins, small-molecule drugs, large-molecule drugs, live cells, and combinations thereof.

11. The method of claim 1, wherein the pill or device includes a separation wall, chamber, or layer configured to maintain multiple therapeutic agents separate until release.

12. The method of claim 1, wherein the therapeutic composition comprises one or more hormones selected from GIP, GLP-1, PYY, motilin, glucagon, amylin, ghrelin, and combinations thereof.

13. The method of claim 1, wherein the pill or device includes an exposed region configured to dissolve in gastric fluid and alter the center-of-mass distribution of the device.

14. The method of claim 13, wherein the exposed region comprises a separation zone configured to divide the device into multiple portions upon dissolution.

15. The method of claim 1, wherein the pill or device is enclosed within a dissolvable capsule and is configured to orient a delivery region toward tissue after release from the capsule.

16. The method of claim 1, wherein the therapeutic composition further comprises an acid-neutralizing component selected from magnesium hydroxide, aluminum hydroxide, sodium bicarbonate, and combinations thereof.

17. The method of claim 1, wherein the pill or device is enclosed within a protective cover configured to descend through gastric fluid and release the therapeutic composition onto tissue as the cover dissolves.

18. The method of claim 1, wherein the therapeutic composition comprises a liquid component and a dry component maintained separately until delivery.

19. The method of claim 1, wherein the pill or device is enclosed within a protective delivery cover having a density sufficient to promote descent through gastric fluid and orientation toward tissue.

20. The method of claim 1, wherein the ballast comprises a dissolvable material that promotes initial descent through gastric fluid and subsequently dissolves, leaving the pill or device with a bulk density of at least 1.04 $g/cm^3$.

21. The method of claim 1, wherein the device exhibits a self-righting moment when tilted due to a center of mass positioned below a geometric center of the device.

22. The method of claim 6, wherein the protective barrier dissolves more slowly than the delivery region and maintains substantially unidirectional release for at least five minutes in simulated gastric fluid.

23. The method of claim 1, wherein the delivery region includes a mucoadhesive polymer configured to retain proximity to stomach tissue.

24. The method of claim 1, wherein the ballast slows movement of the pill or device through the gastrointestinal tract to increase tissue contact time during delivery.

25. The method of claim 1, wherein the delivery region includes one or more microneedles.

* * * * *